(12) United States Patent
Karikomi et al.

(10) Patent No.: US 11,246,475 B2
(45) Date of Patent: Feb. 15, 2022

(54) ENDOSCOPE

(71) Applicant: OLYMPUS CORPORATION, Hachioji (JP)

(72) Inventors: Norihito Karikomi, Tachikawa (JP); Atsushi Watanabe, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 391 days.

(21) Appl. No.: 16/396,161

(22) Filed: Apr. 26, 2019

(65) Prior Publication Data

US 2019/0246885 A1 Aug. 15, 2019

Related U.S. Application Data

(63) Continuation of application No. PCT/JP2017/036504, filed on Oct. 6, 2017.

(30) Foreign Application Priority Data

Nov. 9, 2016 (JP) .............................. JP2016-218983

(51) Int. Cl.
*A61B 1/012* (2006.01)
*A61B 1/018* (2006.01)
(Continued)

(52) U.S. Cl.
CPC .............. *A61B 1/012* (2013.01); *A61B 1/005* (2013.01); *A61B 1/00066* (2013.01); *A61B 1/015* (2013.01); *A61B 1/018* (2013.01)

(58) Field of Classification Search
CPC ... A61B 1/00066; A61B 1/012; A61B 1/0019; A61B 1/00071; A61B 1/005; A61B 1/0055

See application file for complete search history.

(56) References Cited

U.S. PATENT DOCUMENTS 4,280,500 A * 7/1981 Ono .................. A61M 25/0054
                                                                  604/523
4,875,468 A * 10/1989 Krauter .................. A61B 1/015
                                                                  600/153
(Continued)

FOREIGN PATENT DOCUMENTS

JP         H06-041701 U      6/1994
JP         H8-142236 A       6/1996
(Continued)

OTHER PUBLICATIONS

Dec. 19, 2017 International Search Report issued in International Patent Application No. PCT/JP2017/036504.

*Primary Examiner* — Matthew J Kasztejna
(74) *Attorney, Agent, or Firm* — Oliff PLC (57) ABSTRACT

An endoscope including: a flexible sheath extending in a longitudinal direction; a rigid body portion connected to an end portion of the flexible sheath; a ferrule provided in the rigid body portion and having a connection portion; and a tube inserted into the flexible sheath and including an end portion connected to the ferrule. The tube includes: an inner resin layer having a solid structure and that extends along an entire length of the tube in the longitudinal direction; and an outer layer provided on the inner layer and including a first portion that covers at least part of an outer periphery of the connection portion and has a porous structure, and a second portion having a solid structure and that is located on a side of the first portion that is away from the end portion of the tube.

20 Claims, 9 Drawing Sheets

(51) Int. Cl.
*A61B 1/015* (2006.01)
*A61B 1/005* (2006.01)
*A61B 1/00* (2006.01)

(56) References Cited

U.S. PATENT DOCUMENTS

| | | | | | |
|---|---|---|---|---|---|
| 4,967,732 | A | * | 11/1990 | Inoue | A61B 1/00137 600/139 |
| 5,529,820 | A | * | 6/1996 | Nomi | A61L 29/041 428/36.4 |
| 5,735,793 | A | * | 4/1998 | Takahashi | A61B 1/00059 600/104 |
| 5,885,209 | A | | 3/1999 | Green | |
| 6,464,632 | B1 | * | 10/2002 | Taylor | A61B 1/005 138/174 |
| 6,517,571 | B1 | * | 2/2003 | Brauker | A61F 2/06 623/1.13 |
| 7,175,734 | B2 | * | 2/2007 | Stewart | A61B 18/1492 156/290 |
| 8,003,180 | B2 | * | 8/2011 | Goffena | B32B 5/32 428/36.9 |

FOREIGN PATENT DOCUMENTS

| | | |
|---|---|---|
| JP | H8-0211304 A | 8/1996 |
| JP | H10-99263 A | 4/1998 |
| JP | 2001-46314 A | 2/2001 |
| JP | 3184387 B2 | 7/2001 |

* cited by examiner

ENDOSCOPE

CROSS-REFERENCE TO RELATED APPLICATIONS

This application is a Continuation Application of PCT Application No. PCT/JP2017/036504, filed Oct. 6, 2017 and based upon and claiming the benefit of priority from prior Japanese Patent Application No. 2016-218983, filed Nov. 9, 2016, the entire contents of all of which are incorporated herein by reference.

FIELD

The disclosed embodiments relate to an endoscope having a tube inserted through a flexible sheath.

BACKGROUND

A flexible tube of an endoscope can have an inner layer having a solid structure formed of PTFE (polytetrafluoroethylene) and an outer layer having a porous structure.

For example, an endoscope can have a flexible tube through which a fluid can flow. In this flexible tube, the inner layer can have a solid structure formed of PTFE. The outer layer can include a solid structure portion, a transition portion in which the structure gradually changes from solid to porous, and a soft portion having a porous structure.

SUMMARY

An endoscope of the disclosed embodiments includes a flexible sheath extending in a longitudinal direction; a rigid body portion connected to an end portion of the flexible sheath; a ferrule provided in the rigid body portion and having a connection portion; and a tube inserted into the flexible sheath and including an end portion connected to the ferrule. The tube includes: an inner resin layer having a solid structure and that extends along an entire length of the tube in the longitudinal direction; and an outer layer provided on the inner layer and including a first portion that covers at least part of an outer periphery of the connection portion and has a porous structure, and a second portion having a solid structure and that is located on a side of the first portion that is away from the end portion of the tube.

DETAILED DESCRIPTION

Figure 1:
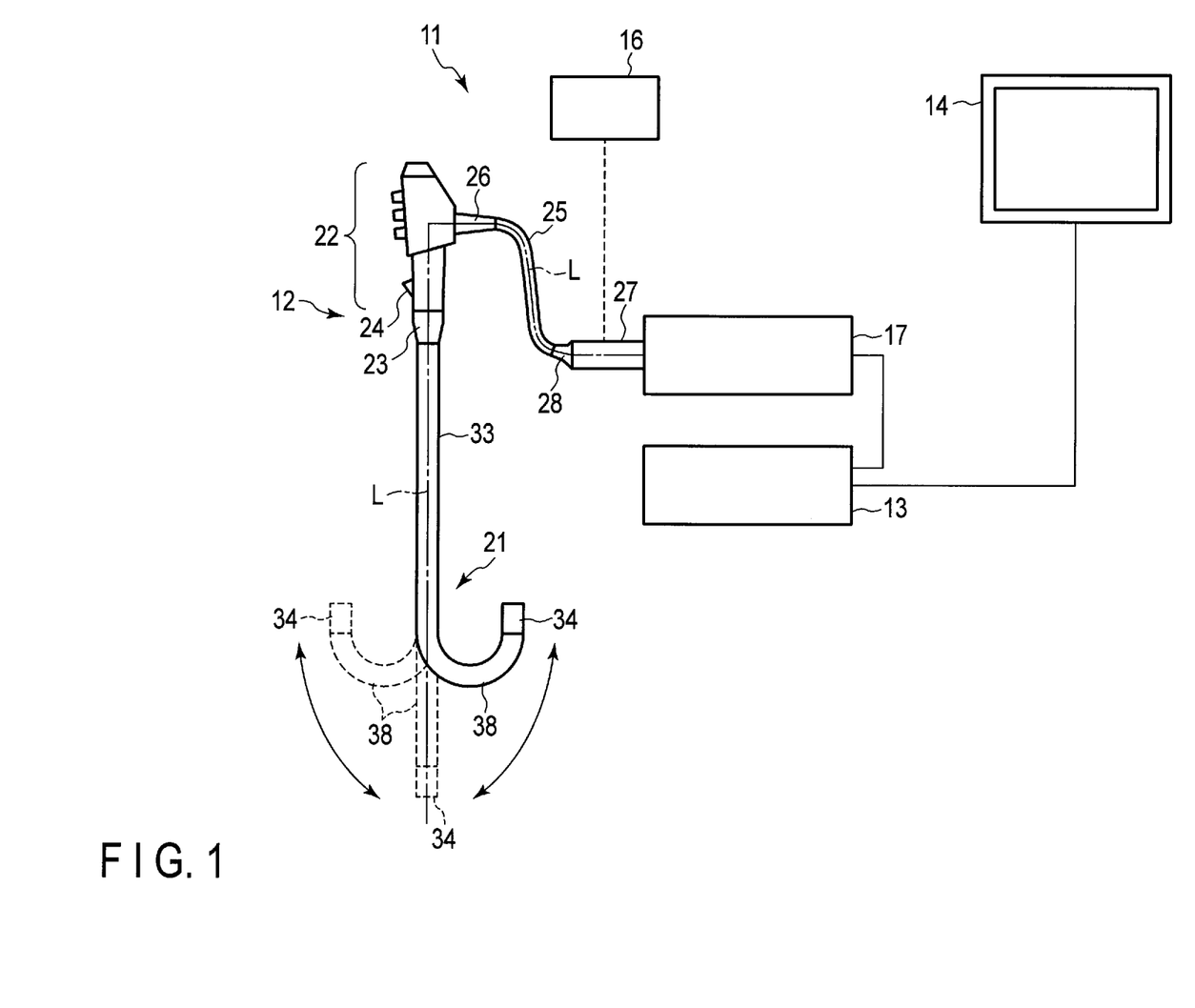
FIG. 1 is a schematic diagram showing an endoscope system and an endoscope according to the disclosed embodiments.
Figure 2:
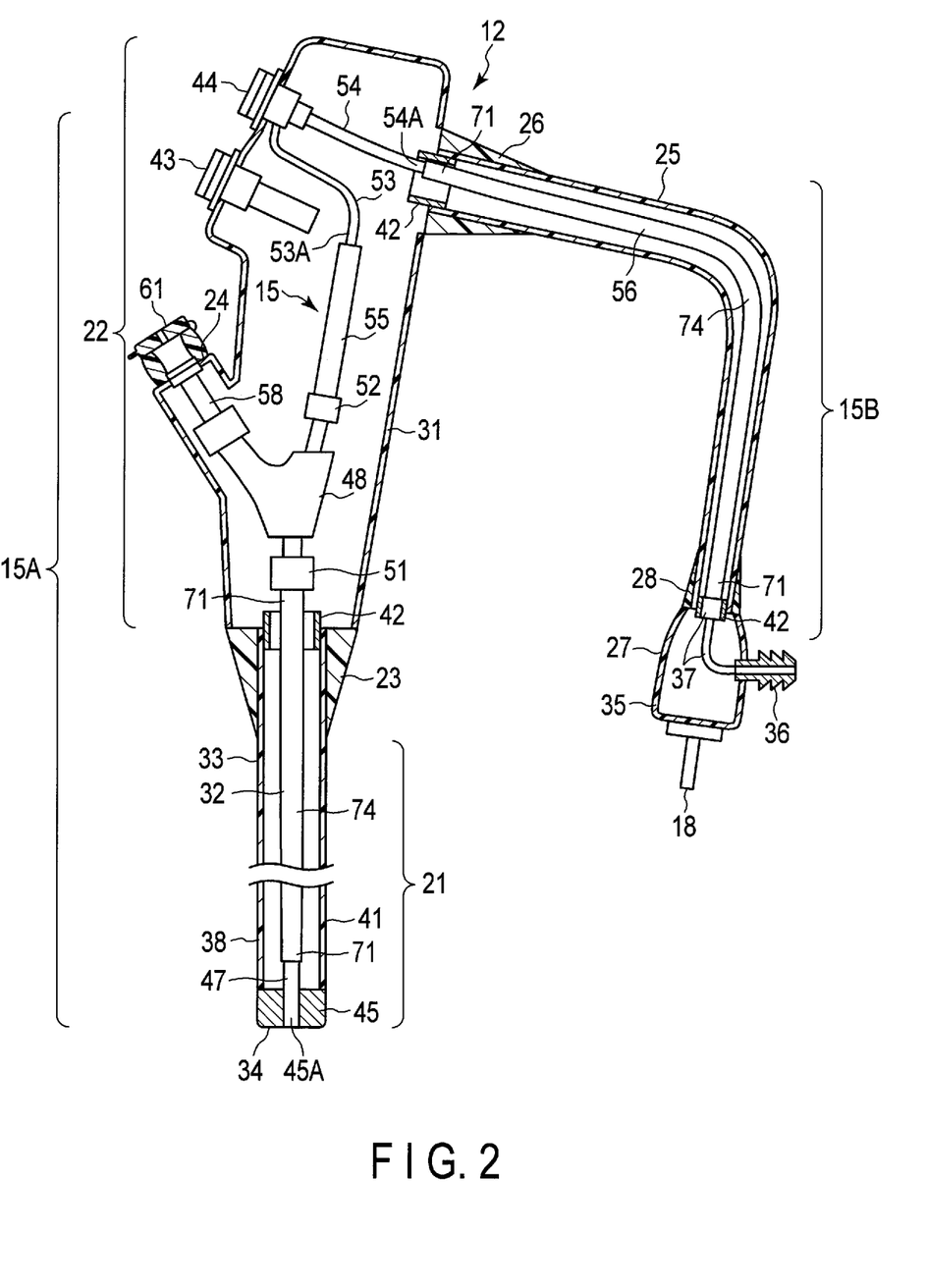
FIG. 2 is an enlarged sectional view showing the endoscope depicted in FIG. 1.

An endoscope system according to the disclosed embodiments will be described with reference to FIG. 1 to FIG. 7. As shown in FIGS. 1 and 2, the endoscope system 11 includes an endoscope 12, an endoscope controller 13 (control unit) which performs image processing based on a subject image captured by the endoscope 12, a display unit 14 (monitor) which displays an image generated by image processing performed by the endoscope controller 13, a suction unit 16 (vacuum pump) connected to a suction path 15 formed in the endoscope 12 and for sucking a fluid (air, liquid) into the suction path 15, and a light source 17 which supplies illumination light to an illumination optical system to be described later.

As shown in FIGS. 1 and 2, the endoscope 12 includes an insertion section 21 to be inserted into a duct such as a lumen of a subject along a longitudinal direction L (along a central axis of the insertion portion), an operation section 22 provided on the proximal end side of the insertion section 21 and gripped by an operator during operation, a first bending preventing portion 23 provided on the proximal side of the insertion section 21 and located at a position adjacent to the operation section 22, a treatment instrument introduction portion 24 provided for the operation section 22 at a position on the side of the insertion section 21, a universal cord 25 extending from the operation section 22 toward the endoscope controller 13, a second bending preventing portion 26 provided on the proximal side of the universal cord 25 and located at a position adjacent to the operation section 22, a connector 27 provided at the distal end portion of the universal cord 25 and constituting a connection portion between the universal cord 25 and the endoscope controller 13, a third bending preventing portion 28 provided on the distal end side of the universal cord 25 and located at a position adjacent to the connector 27, and a suction path 15 that extends from the distal end of the insertion section 21 to the connector 27 via the operation section 22 and the universal cord 25. The operation section 22 has an operation section case 31 constituting the outer shell thereof. The operation section 22 is an example of a rigid body portion.

The first bending preventing portion 23 is formed of a flexible resin material and shaped like a hollow truncated cone. A through hole is defined in the first bending preventing portion 23 so that various piping and wiring, such as the first suction tube 32 of the suction path 15, can pass therethrough. The thickness of the first bending preventing portion 23 increases as it approaches the operation section 22, and the rigidity increases (the flexibility decreases) as it approaches the operation section 22. The first bending preventing portion 23 can be greatly deformed at a position (distal end side) close to the distal end structure portion 34 such that it can follow the curvature of the pipe portion 33 of the insertion section 21. Therefore, when the operator grasps the endoscope 12 and bends the pipe portion 33, the distal end side of the first bending preventing portion 23 can be greatly deformed and thus receives the force applied to the pipe portion 33. As a result, the first bending preventing portion 23 can distribute the force applied concentratedly on the proximal side of the pipe portion 33 of the insertion section 21 toward the distal end side in the longitudinal direction L. Further, the first bending preventing portion 23 can prevent the pipe portion 33 from being broken and can gradually change the flexibility of the pipe portion 33 along the longitudinal direction L.

As shown in FIG. 2, the connector 27 includes a connector case 35, a connection portion 36 provided so as to project outward from the connector case 35, a terminal 18 for connection between the endoscope controller 13 and the light source section, and a fourth ferrule provided inside the connector case 35 so as to be interposed between the suction path 15 and the connection portion 36. The connection portion 36 is connected to the suction path 15. The connector 27 is an example of a rigid body portion.

As shown in FIG. 1, the insertion section 21 includes a distal end structure portion 34, a bendable portion 38 and a pipe portion 33 in order from the distal end to the proximal end. The pipe portion 33 is flexible in the case of a so-called flexible endoscope. The bendable portion 38 can be bent in a plurality of directions, e.g., two or four directions, by a known mechanism employing a towing wire 39 (see FIG. 6) or the like when a rotation knob (not shown) provided on the operation section 22 is operated. The bendable portion 38, the pipe portion 33, and the universal cord 25 are examples of flexible sheaths extending from the operation section 22 in the longitudinal direction L. The bendable portion 38 and the pipe portion 33 each have a tubular outer skin 41 for covering and protecting an internal structure. The outer skin 41 is formed of a synthetic resin material or the like and is continuously provided from the distal end structure portion 34 to a connection ferrule 42 provided at the end portion of the operation section 22. A metal reinforcing member (spiral pipe) integrally provided with the outer skin 41 may be provided inside the outer skin 41.

As shown in FIGS. 1 and 2, the endoscope 12 is provided with an illumination optical system for illuminating the interior of the subject, and an objective optical system including an imaging unit, an objective lens, etc.

Although not shown, the endoscope is provided with an air/water supply mechanism for supplying a fluid toward an examination portion in the subject. The air/water supply mechanism includes an air/water supply channel formed in the distal end structure portion 34. The air/water supply mechanism is operated with a first button 43 of the operation section. The suction unit 16 communicates with the suction path 15 and is operated with a second button 44 of the operation section 22.

The illumination optical system and the objective optical system are inserted through the insertion section 21 (the distal end structure portion 34, the bendable portion 38, and the pipe portion 33), the operation section 22, and the universal cord 25. The illumination optical system has a light guide fiber bundle inserted inside the bendable portion 38 and the universal cord 25, and an illumination lens connected to the distal end of the light guide fiber bundle.

Figure 6:
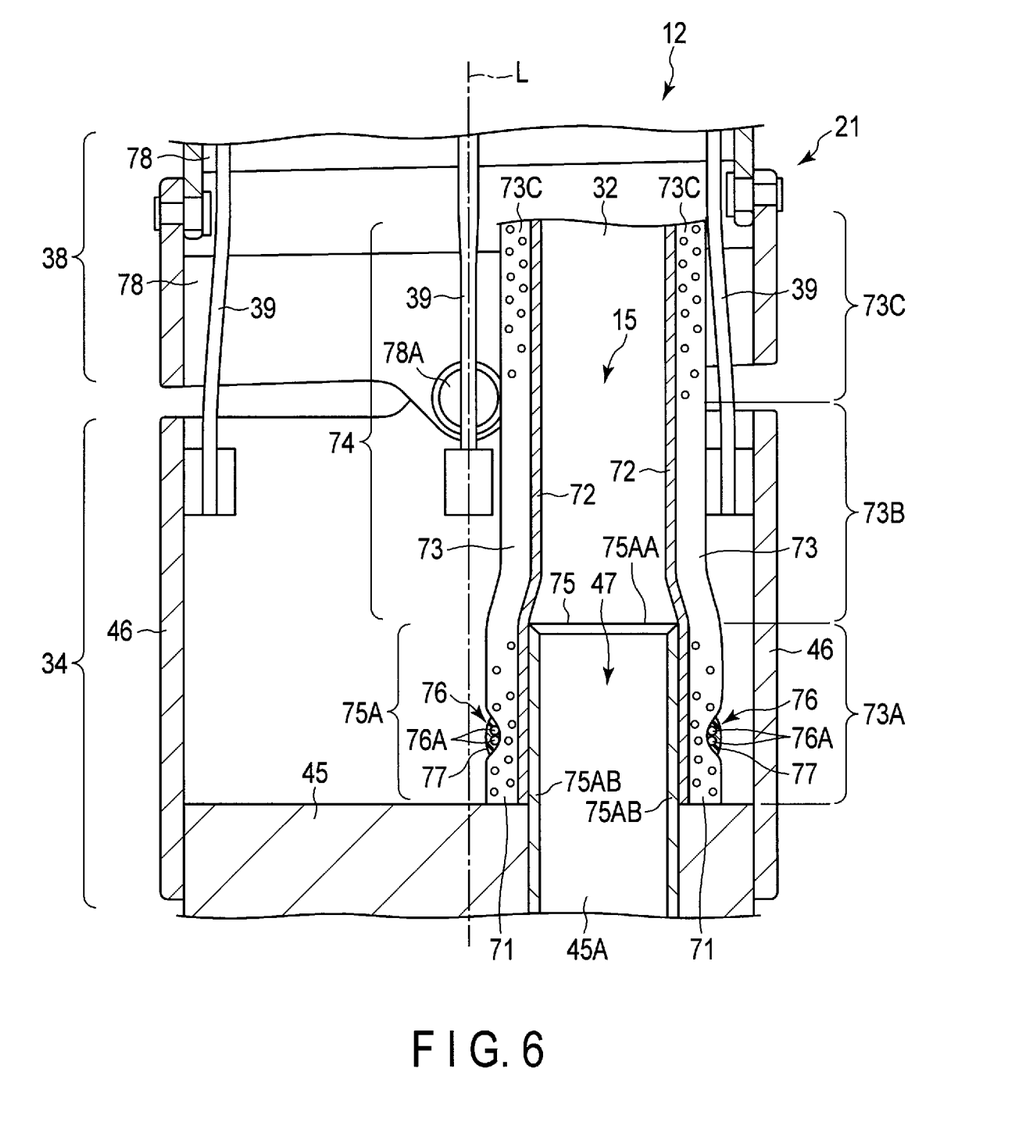
FIG. 6 is an enlarged sectional view showing the first ferrule depicted in FIG. 2.

As shown in FIG. 6, the distal end structure portion 34 includes a distal end structure main body 45 and an outer pipe portion 46 extending from the distal end structure main body 45 toward the bendable portion 38. The distal end structure portion 34 (the distal end structure main body 45 and the outer pipe portion 46) is an example of a rigid body portion.

Figure 3:
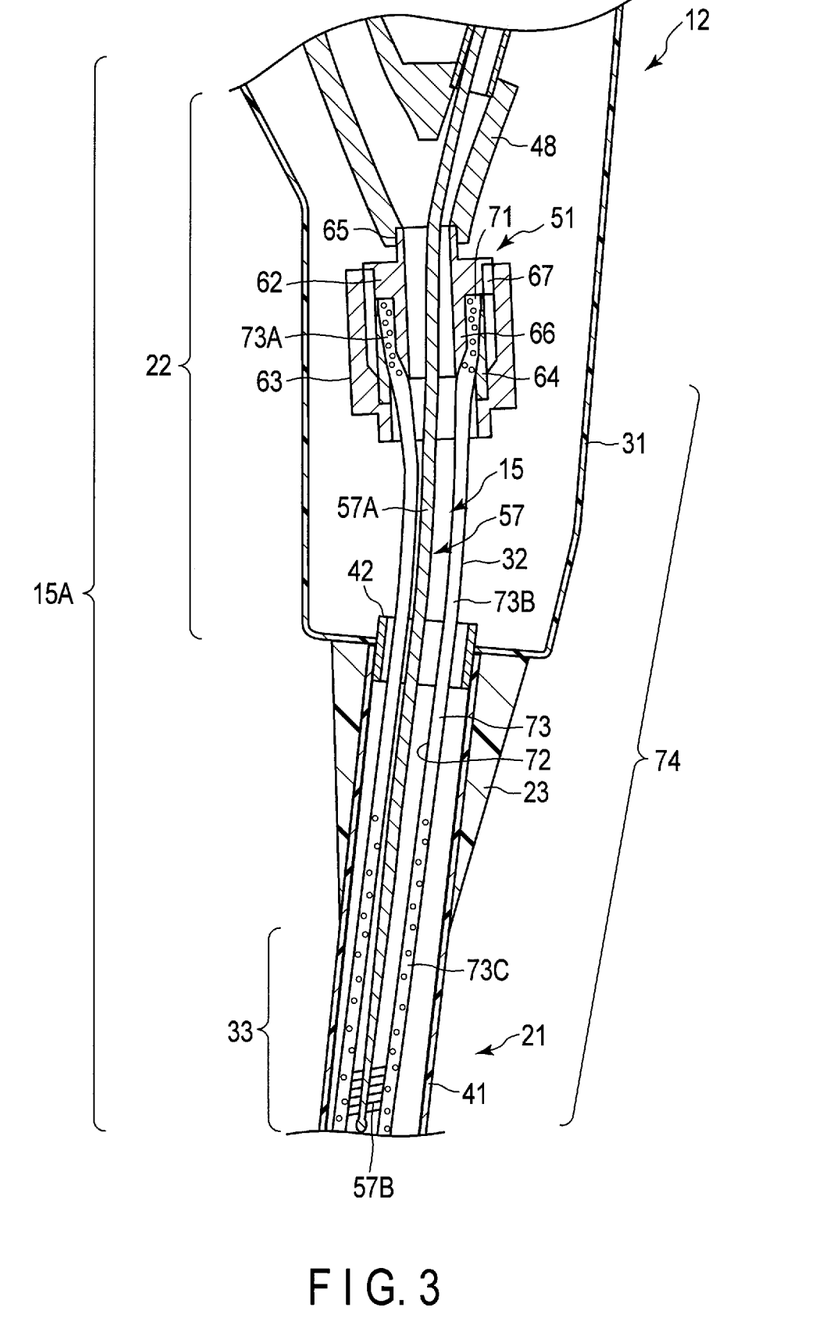
FIG. 3 is a sectional view showing an operation section, a first bending preventing portion, and an insertion section of the endoscope depicted in FIG. 2.

As shown in FIGS. 2 and 3, the suction path 15 includes a through hole 45A formed in the distal end structure main body 45, a cylindrical first ferrule 47 formed so as to be continuous with the through hole 45A, a branch portion 48 having an internal flow path branched into a "Y" shape inside the operation section 22, a tubular second ferrule 51 provided at the outlet of the branch portion 48 on the side of the insertion section 21, a tubular third ferrule 52 provided at the output of the branch portion 48 on the side of the universal cord 25, a tubular fourth ferrule 37 provided inside the connector 27, a first suction conduit 53 provided in the operation section 22 and connected to the side surface of the second button 44, a second suction conduit 54 provided in the operation section 22 and connected to the bottom of the second button 44, a first suction tube 32 (treatment instrument insertion channel) inserted into the insertion section 21 and connecting the first ferrule 47 and the second ferrule 51, a second suction tube 55 provided in the operation section 22 so as to connect the third ferrule 52 and the distal end portion 53A of the first suction conduit 53, and a third suction tube 56 inserted into the universal cord 25 so as to connect the distal end portion 54A of the second suction conduit 54 and the fourth ferrule 37 of the connector 27. The first suction conduit 53 and the second suction conduit 54 are made of, for example, metallic pipes. The second ferrule 51 is an example of a ferrule provided in a rigid body portion.

When the operator presses the second button 44, the negative pressure of the suction unit 16 has an effect on the through hole 45A of the distal end structure portion 34. As a result, a suctioned matter is sucked toward the suction unit 16 via the suction path, that is, from the distal end of the insertion section 21 to the connector 27 via the operation section 22 and the universal cord 25.

The suction path 15 includes two kinds of paths for passing a washing brush 57 when the interior is washed. As the washing brush 57, the brush having the structure shown in FIG. 3 is used by way of example. This washing brush 57 includes a flexible shaft portion 57A obtained by winding a metal element wire in the form of a coil, and a brush portion 57B provided at the distal end portion of the shaft portion 57A and having a plurality of washing bristles.

As shown in FIG. 2, the first path 15A is a path that passes the brush 57 from the second button 44 to the first suction conduit 53. By passing the brush 57 through the first path 15A, the interiors of the first suction conduit 53, the second suction tube 55, the third ferrule 52, the branch portion 48, the second ferrule 51, the first suction tube 32, the first ferrule 47, and the through hole 45A can be washed. The second path 15B is a path for passing the brush 57 from the second button 44 to the second suction conduit 54. By passing the brush 57 through the second path 15B, the interiors of the second suction conduit 54, the third suction tube 56, the fourth ferrule 37, and the connection portion 36 can be washed.

The endoscope 12 is provided with a cylindrical treatment instrument introduction ferrule 58, and the treatment instrument introduction ferrule 58 is connected to the outlet of the treatment instrument introduction portion 24 of the branch portion 48. An openable/closable member referred to as a forceps plug 61 can be attached to the treatment instrument introduction ferrule 58. In the state where a treatment instrument is not inserted into the treatment instrument introduction ferrule 58, the treatment instrument introduction ferrule 58 is sealed with the forceps plug 61.

Figure 4:
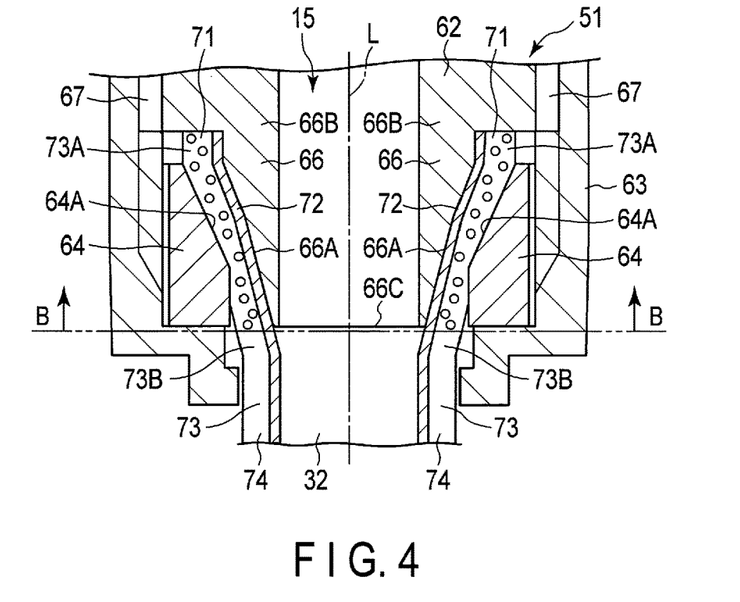
FIG. 4 is an enlarged sectional view showing the second ferrule depicted in FIG. 3.

As shown in FIGS. 3 and 4, the second ferrule 51 includes a second ferrule main body 62, a nut portion 63 engageable with the second ferrule main body 62, and an annular pressing ring 64 provided between the second ferrule main body 62 and the nut portion 63. The second ferrule main body 62 includes a branch side fixing portion 65 connected to the branch portion 48 by soldering or the like, a connection portion 66 on which the first suction tube 32 is covered, and a second screw portion 67 provided between the connection portion 66 and the branch side fixing portion 65 and engaged with the nut portion 63. The connection portion 66 includes a tapered portion 66A provided in the vicinity of the distal end.

The pressing ring 64 includes an inner circumferential surface 64A expanded toward the proximal end 66B of the connection portion 66 so as to follow the shape of the tapered portion 66A. The second ferrule 51 can clamp (fix) the first suction tube 32 between the tapered portion 66A and the inner circumferential surface 64A. In this fixed state, the pressing ring 64 squeezes substantially the entire outer peripheral surface of the end portion 71 of the first suction tube 32.

Figure 5:
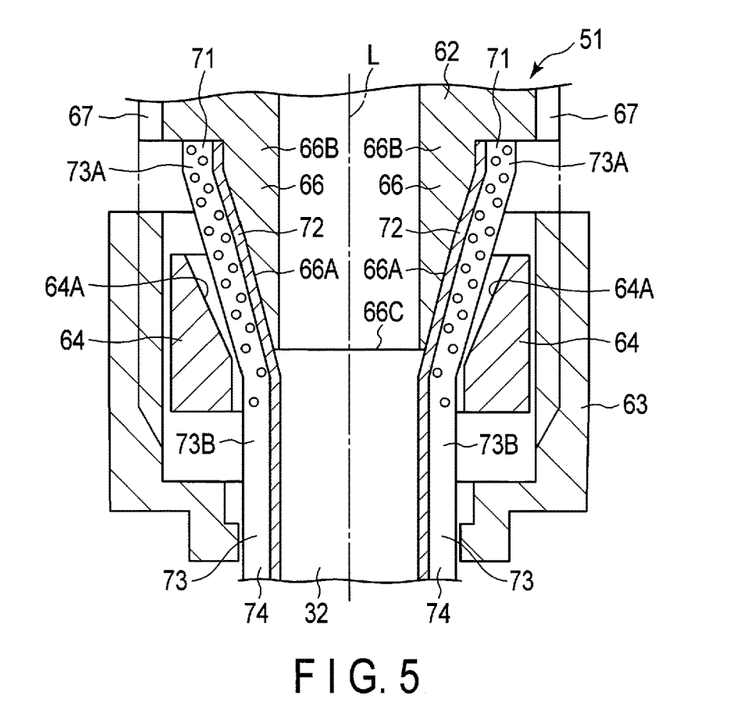
FIG. 5 is a sectional view illustrating a step in which a first suction tube, a pressing ring, and a nut part are fixed to the second mouth-ring main body of the second ferrule depicted in FIG. 4.

As shown in FIGS. 3 to 5, the first suction tube 32 is formed, for example, to have an inner diameter of 1 to 6 mm and a thickness of 0.2 to 1.0 mm. The first suction tube 32 has a two-layer structure including an inner layer 72 and an outer layer 73 provided outside the inner layer 72 and integrally joined to the inner layer 72. The inner layer 72 and the outer layer 73 are made of a resin containing a fluorocarbon resin (PTFE) at least partially, but may be formed of the fluorocarbon resin (PTFE) entirely.

The outer layer 73 of the first suction tube 32 may be made of a resin other than a fluorine-containing resin, for example a thermoplastic resin such as polyurethane, polyethylene, polypropylene, polystyrene, or polyvinyl chloride. The inner layer 72 and the outer layer 73 may be joined using an adhesive.

As shown in FIGS. 3 to 6, the first suction tube 32 includes a pair of end portions 71 (a distal end portion and a proximal end portion) and an intermediate portion 74 located between the end portions 71. The intermediate portion 74 is intended to refer to an intermediate portion of the first suction tube 32 that is other than the end portions 71. One of the end portions 71 covers the outer periphery of the first ferrule 47 and is connected to the first ferrule 47, and the other one of the end portions 71 covers the outer periphery of the connection portion 66 and is connected to the second ferrule 51. The inner layer 72 is made of a resin (e.g., PTFE) that has a solid structure over the entire length in the longitudinal direction L.

The outer layer 73 is provided with a pair of first portions 73A provided in the vicinity of end portions 71 and are made of a resin having a porous structure, a second portion 73B located at a side more away from the end portions 71 along the longitudinal direction L than the first portions 73A and made of a resin having a solid structure, and a third portion 73C located at a side more away from the end portions 71 along the longitudinal direction L than the second portion 73B and made of a resin having a porous structure. The first portions 73A and the second portion 73B are arranged inside the operation section 22 (rigid body portion). Although part of the second portion 73B is arranged inside the first bending preventing portion 23, as will be described later, the portion of the first bending preventing portion 23 on the side of the operation section 22 can be regarded as a rigid body portion.

The structure of the first suction tube 32 will be further described, taking the vicinity of the second ferrule 51 as an example. As shown in FIGS. 3 and 4, the first portion 73A can extend along the entire length of the tube 32 covering the connection portion 66 of the second ferrule 51. The first portion 73A may extend from the proximal end 66B of the connection portion 66 to at least the distal end 66C of the connection portion 66. For example, a boundary between the first portion 73A and the second portion 73B can be positioned at (coincides with) the distal end 66C of the connection portion 66, as shown in FIG. 4. The third portion 73C constitutes at least part of the intermediate portion 74. The third portion 73C is arranged inside the bendable portion 38 and the pipe portion 33 (flexible sheath).

The porosity of the first portion 73A and the third portion 73C which have a porous structure is, for example, 20 to 70%, more preferably 30 to 60%. The porosity is defined as the ratio of the volume of the pore portions (cavity portions) to the total volume of the base resin.

As shown in FIG. 4, the end portion 71 of the first suction tube 32 is fixed to the connection portion 66 in such a manner as to cover the periphery of the connection portion 66 of the second ferrule 51. The end portion 71 of the first suction tube 32 is fixed to the outer periphery of the connection portion 66 in an expanded state (i.e., the diameter of end portion 71 of the first suction tube 32 is stretched radially outward). A boundary line B-B between the first portion 73A of the outer layer 73 of the first suction tube 32 and the second portion 73B thereof is provided to coincide with the distal end 66C of the connection portion 66 of the second ferrule 51.

As shown in FIG. 3 and FIG. 4, the second portion 73B is provided at an intermediate position between the distal end 66C of the connection portion 66 of the second ferrule 51 and the first bending preventing portion 23. The third portion 73C is formed on that side of the first bending preventing portion 23 which is away from the end portion 71 along the longitudinal direction L. The boundary between the second portion 73B and the third portion 73C is located inside the first bending preventing portion 23.

As shown in FIG. 4, in a state where the nut portion 63 is engaged (fixed) with the second ferrule main body 62, the first suction tube 32 is compressed between the connection portion 66 of the second ferrule main body 62 and the pressing ring 64. As a result, the first suction tube 32 is fixed to the second ferrule main body 62 in a watertight manner. The nut portion 63 and the pressing ring 64 constitute an example of a compression portion that compresses the first suction tube 32 against the second ferrule 51 and fixes the first suction tube 32 to the second ferrule 51. The nut portion 63 and the pressing ring 64 also constitute an example of a tube fixing portion that has a pipe (tubular member) for compressing the first suction tube 32 against the second ferrule 51.

With this structure, the first suction tube 32 can be easily removed, so that the first suction tube 32 can be repaired alone. Further, the second portion 73B of the solid structure is provided at an intermediate position between the distal end 66C of the connection portion 66 of the second ferrule 51 and the first bending preventing portion 23. Therefore, even if the inner layer 72 is scraped when washing is performed with the washing brush 57 inserted into the first suction tube 32 or when a treatment instrument is repeatedly inserted into the first suction tube 32, the second portion 73B is located outward of the inner layer 72 and air tightness is ensured thereby. Thus, the first suction tube 32 is prevented from being damaged at an intermediate position between the distal end of the connection portion 66 of the second ferrule 51 and the first bending preventing portion 23.

The intermediate portion between the distal end of the connection portion 66 of the second ferrule 51 and the first bending preventing portion 23 is partly located inside the operation section 22, and the remaining part is located inside the first bending preventing portion 23. Therefore, even when a bending load is applied to the insertion section 21 (the pipe portion 33) by the operator, the bending load is hardly applied to the first suction tube 32 at the intermediate position between the distal end of the connection portion 66 of the second ferrule 51 and the first bending preventing portion 23, or the bending load is applied at only a small angle. For this reason, although the second portion 73B of the solid structure is less flexible than the other porous structure portions, this does not cause a problem in practice. Since the third portion 73C is formed of a porous structure and is sufficiently flexible, the first suction tube 32 is not broken at the bendable portion 38 or the pipe portion 33 even if the third portion 73C is repeatedly bent at such portions.

A method of fixing the first suction tube 32 to the second ferrule 51 will be briefly described with reference to FIG. 5. In the state where the end portion of the first suction tube 32 is expanded by means of a jig, the connection portion 66 of the second ferrule main body 62 is attached to the first suction tube 32. By so doing, the first suction tube 32 covers the connection portion 66 without any gap. In this state, the pressing ring 64 and the nut portion 63 are fastened to the second ferrule main body 62, so that the first suction tube 32 is compressed between the pressing ring 64 and the connection portion 66. At this time, since the first portion 73A (porous structure) of the outer layer 73 of the first suction tube 32 is arranged at a position between the pressing ring 64 and the connection portion 66, the first suction tube 32 is easily deformable at this portion, and the first suction tube 32 can be compressed with a relatively small force.

Next, the structure of the first suction tube 32 around the first ferrule 47 located opposite to the second ferrule 51 will be described. As shown in FIG. 6, the first ferrule 47 includes a first ferrule main body 75 integrally formed with the distal end structure portion 34, a connection portion 75A provided on the first ferrule main body 75, and a thread winding portion 76 for fixing the first suction tube 32 to the first ferrule main body 75. The first ferrule main body 75 protrudes from the distal end structure main body 45 toward the operation section 22. The end portion 71 of the first suction tube 32 covers the connection portion 75A of the first ferrule 47 from the outside. The first ferrule main body 75 (connection portion 75A) has a length of 3 to 10 mm, for example. As shown in FIG. 6, the end portion 71 of the first suction tube 32 (i.e., the end portion located opposite to the end portion on the side of the operation section 22) is fixed to the connection portion 75A in such a manner as to cover the periphery of the connection portion 75A of the first ferrule 47. The end portion 71 of the first suction tube 32 is fixed to the outer periphery of the connection portion 75A in an expanded state.

The thread winding portion 76 is provided on the outer peripheral portion of the end portion 71 of the first suction tube 32. The thread winding portion 76 includes a thread 76A wound around the outer periphery of the first suction tube 32, and an adhesive 77 sealing the surface of the thread 76A. The thread winding portion 76 enables the end portion 71 of the first suction tube 32 to be fixed to the first ferrule main body 75 in a watertight manner. The thread winding portion 76 is an example of a compression portion that compresses the first suction tube 32 against the first ferrule 47 and fixes the first suction tube 32 to the first ferrule 47. In this fixed state, the thread winding portion 76 squeezes only part of the outer peripheral surface of the end portion 71 of the first suction tube 32.

The first portion 73A of the outer layer 73 of first suction tube 32 is provided to correspond to the entire connection portion 75A of the first ferrule 47. The second portion 73B of the outer layer 73 extends from the proximal end 75AA of the first ferrule 47 to the first rotation pin 78A (the pin closest to the distal end structure portion) of the bending piece 78 incorporated in the bendable portion 38. The portion from the proximal end 75AA of the first ferrule 47 to the first rotation pin 78A can be rephrased as a portion which corresponds to the distal end structure portion 34 and which is more away from the end portion 71 of the first suction tube 32 along the longitudinal direction L than the proximal end 75AA of the first ferrule 47. The first portion 73A and the second portion 73B are disposed inside the distal end structure portion 34 (rigid body portion) constituted by the distal end structure main body 45 and the outer pipe portion 46.

A plurality of pins including the first rotation pin 78A enable bending pieces to be rotated in a predetermined direction and thus constitute a joint for bending the bendable portion 38. The plurality of pins including the first rotation pin 78A are made of rivets, for example. The third portion 73C of the outer layer 73 is provided to correspond to a position which is more away from the end portion 71 of the first suction tube 32 along the longitudinal direction L than the first rotation pin 78A. The third portion 73C is arranged inside the bendable portion 38 (flexible sheath).

With this structure, the second portion 73B of the solid structure is disposed at a position which corresponds to the distal end structure portion 34 and which is more away from the end portion 71 of the first suction tube 32 along the longitudinal direction L than proximal end 75AA of the first ferrule 47. Therefore, even if the inner layer 72 is scraped when washing is performed with the washing brush 57 inserted into the first suction tube 32 or when a treatment instrument is repeatedly inserted into the first suction tube 32, the second portion 73B is located outward of the inner layer 72 and air tightness is ensured thereby. Thus, the first suction tube 32 is prevented from being broken at a position which corresponds to the distal end structure portion 34 and which is more away from the end portion 71 of the first suction tube 32 along the longitudinal direction than the proximal end 75AA of the first ferrule 47.

Even when the bendable portion 38 is bent, bending is hardly applied to that portion of the first suction tube 32 which corresponds to the distal end structure portion 34 and which is more away from the end portion 71 of the first suction tube 32 along the longitudinal direction L than the proximal end 75AA of the first ferrule 47. For this reason, although the second portion 73B of this solid structure is less flexible than the other porous structure portions, this does not cause a problem in practice.

Further, the first portion 73A (porous structure) of the outer layer 73 of the first suction tube 32 is disposed around the periphery of the first ferrule 47 such that the first portion 73A is located between the thread winding portion 76 and the first ferrule 47. Because of this, the first suction tube 32 can be easily deformed at this portion. For this reason, when this portion of the first suction tube 32 is compressed with the thread 76A, this can be accomplished with a comparatively small force. In addition, since the first portion 73A of the outer layer 73 of the first suction tube 32 is deformed and tightened, the outer diameter of the thread winding portion 76 can be reduced. Therefore, the outer diameter of the distal end structure portion 34 can be reduced. The second suction tube 55 has substantially the same structure as the first suction tube 32 and is formed of the same material as the first suction tube 32.

Next, the third suction tube 56 located around the fourth ferrule 37 will be described. The third suction tube 56 has substantially the same structure as the first suction tube 32 and is formed of the same material as the first suction tube 32. For this reason, the respective portions of the third suction tube 56 will be referred to using the same names and reference numerals as the first suction tube 32. The fourth ferrule 37 located in the connector 27 shown in FIG. 2 has substantially the same structure as the second ferrule 51. Therefore, the respective portions of the fourth ferrule 37 will be referred to using the same names and reference numerals as the second ferrule 51, and a detailed illustration of the fourth ferrule 37 is omitted.

The first portion 73A of the outer layer 73 of the third suction tube 56 is provided to correspond to the connection portion 66 of the fourth ferrule 37. The second portion 73B of the outer layer 73 of the third suction tube 56 is provided at an intermediate position between the distal end 66C of the connection portion 66 of the fourth ferrule 37 and the third bending preventing portion 28. Therefore, the first portion 73A and second portion 73B of the outer layer 73 of the third suction tube 56 are disposed inside the connector 27 (rigid body portion).

Although part of the second portion 73B is arranged inside the third bending preventing portion 28, the portion of the third bending preventing portion 28 on the side of the connector 27 can be regarded as a rigid body portion. The length of the second portion 73B of the third suction tube 56 can be properly set in the range of 3 to 10 mm, for example.

The third portion 73C of the outer layer 73 of the third suction tube 56 extends from an intermediate position on the third bending preventing portion 28 along the longitudinal direction L to a position away from the end portion 71 of the tube. For this reason, the third portion 73C of the outer layer 73 of the third suction tube 56 is disposed inside the universal cord 25 (flexible sheath). The third bending preventing portion 28 has substantially the same structure as the first bending preventing portion 23.

The third bending preventing portion 28 has a greater rigidity (a smaller flexibility) as it approaches the connector 27. The third bending preventing portion 28 can prevent the universal cord 25 (flexible sheath) from being broken and can gradually change its flexibility along the longitudinal direction. The third suction tube 56 located around the fourth ferrule 37 can be fixed to the fourth ferrule 37 in the same manner as the first suction tube 32 located around the second ferrule 51 and functions in a similar manner to that of the first suction tube 32 located around the second ferrule 51.

Figure 7:
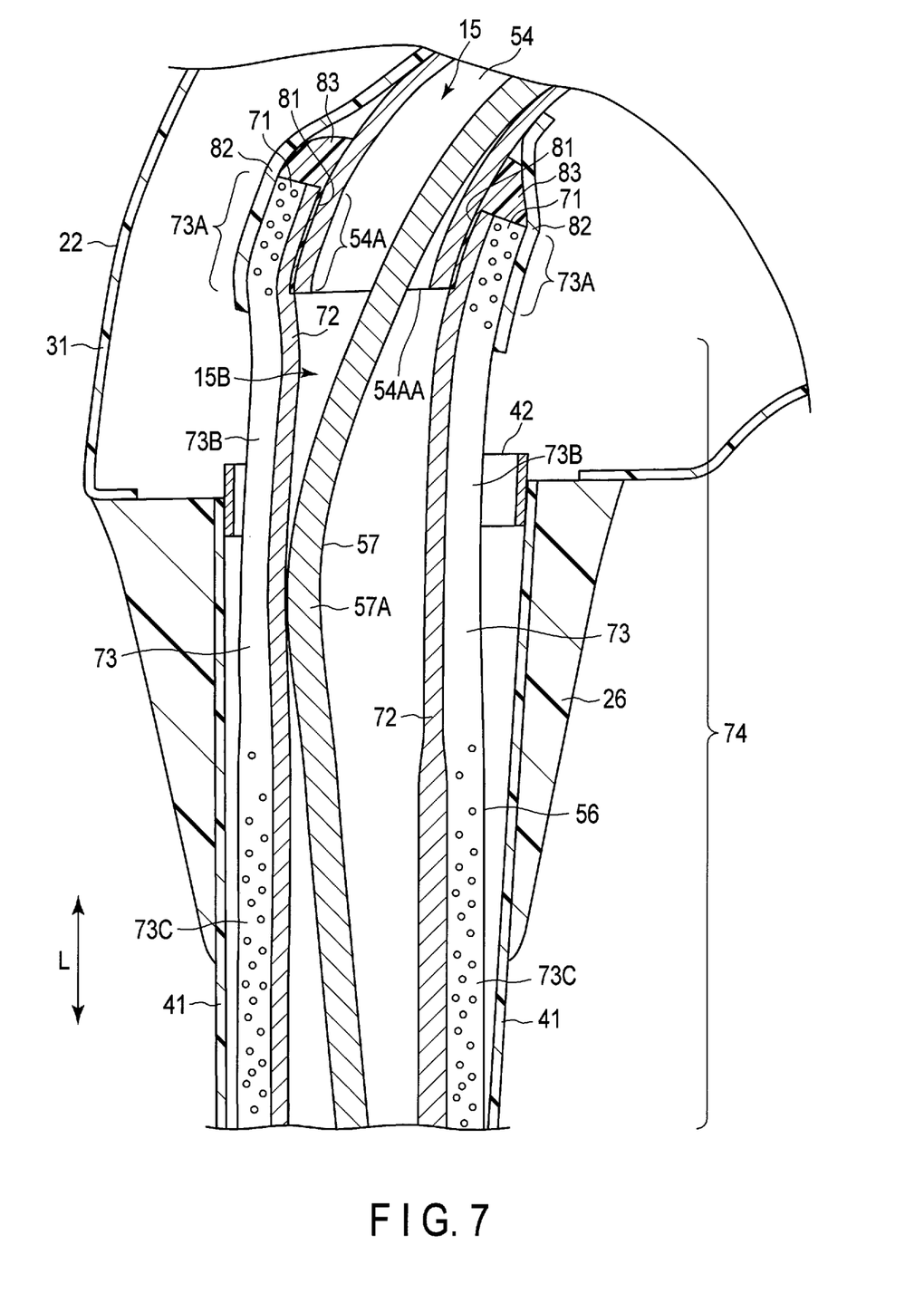
FIG. 7 is an enlarged sectional view showing the distal end portion of the second suction conduit depicted in FIG. 2.

The third suction tube 56 in the vicinity of the distal end portion 54A of the second suction conduit 54 will be described with reference to FIG. 7. The outer layer 73 of the third suction tube 56 is provided with a first portion 73A provided at the end portion 71 and having a porous structure, a second portion 73B located at a side more away from the end portion 71 along the longitudinal direction L than the first portion 73A and having a solid structure, and a third portion 73C located at a side more away from the end portion 71 along the longitudinal direction L than the second portion 73B and having a porous structure. The third portion 73C constitutes at least part of the intermediate portion 74.

The end portion 71 of the third suction tube 56 is fixed to the distal end portion 54A in such a manner as to cover the periphery of the distal end portion 54A of the second suction conduit 54. The end portion 71 of the third suction tube 56 is fixed to the outer periphery of the distal end portion 54A of the second suction conduit 54 in an expanded state. An adhesive 81 is interposed between the distal end portion 54A of the second suction conduit 54 and the third suction tube 56, and the second suction conduit 54 and the third suction tube 56 are fixed to each other in a watertight manner by the adhesive 81.

A heat-shrinkable tube 82 is disposed on the outer periphery of the connection portion by which the second suction conduit 54 and the third suction tube 56 are connected. The heat-shrinkable tube 82 is formed of a heat-shrinkable resin material and can seal the periphery of the connection portion. When shrunk by heat, the heat-shrinkable tube 82 can cover and protect the connection portion. The heat-shrinkable tube 82 is an example of a tube fixing portion provided on the outer periphery of the third suction tube 56 and having a pipe (tubular member) that compresses the third suction tube 56 against the fourth ferrule 37.

An adhesive reservoir 83 is provided in a region surrounded by the side surface of the second suction conduit 54, the end surface of the third suction tube 56, and the heat-shrinkable tube 82. The adhesive reservoir 83 prevents a fluid from leaking out at the connection portion, and firmly fixes the second suction conduit 54 and the third suction tube 56.

The first portion 73A of the outer layer 73 of the third suction tube 56, which has a porous structure, is provided to correspond to the distal end portion 54A (connection portion) of the second suction conduit 54. The second portion 73B of the outer layer 73, which has a solid structure, extends from the tip 54AA of the distal end portion 54A of the second suction conduit 54 to a position corresponding to an intermediate position of the second bending preventing portion 26. Therefore, the first portion 73A and second portion 73B of the outer layer 73 of the third suction tube 56 are disposed inside the operation section 22 (rigid body portion). Although part of the second portion 73B is arranged inside the third bending preventing portion 28, the portion of the third bending preventing portion 28 on the side of the operation section 22 can be regarded as a rigid body portion.

The third portion 73C of the outer layer 73, which has a porous structure, is formed from the intermediate position of the second bending preventing portion 26 and extends away from the end portion 71 of the tube along the longitudinal direction L. For this reason, the third portion 73C of the outer layer 73 of the third suction tube 56 is arranged inside the universal cord 25 (flexible sheath). The boundary between the second portion 73B and the third portion 73C is located inside the second bending preventing portion 26. The second bending preventing portion 26 has substantially the same structure as the first bending preventing portion 23. The second bending preventing portion 26 has a greater rigidity (a lower flexibility) as it approaches the operation section 22.

With this structure, the second portion 73B of the solid structure is disposed at a position which is more away from the end portion 71 of the third suction tube 56 along the longitudinal direction L than the tip 54AA of the distal end portion 54A (connection portion) of the second suction conduit 54. With this structure, even if the inner layer 72 is scraped when washing is performed with the washing brush 57 inserted into the third suction tube 56, the second portion 73B is located outward of the inner layer 72 and air tightness is ensured thereby. Therefore, the third suction tube 56 is prevented from being damaged at a position which is more away from the end portion 71 of the third suction tube 56 along the longitudinal direction L than the tip 54AA of the distal end portion 54A of the second suction conduit 54.

Even when the universal cord 25 is bent, bending is hardly applied to the second suction tube 55 at a position corresponding to the second portion 73B of the outer layer 73. For this reason, the second portion 73B of this solid structure is less flexible than the other porous structure portions, but this does not cause a problem in practice.

The endoscope 12 described above has improved durability. Ordinarily, if washing is repeatedly performed with the washing brush 57 inserted into the tube, the inner layer 72 may be scraped off by the repeated sliding movement of the washing brush 57. In this case, sufficient air tightness and liquid tightness are hard to maintain with only the outer layer 73 of the porous structure. According to the above structure, however, the second portion 73B of the outer layer 73 of the solid structure can be arranged at a portion with which the washing brush easily comes into contact (i.e., at a position which is more away from the end portion 71 along the longitudinal direction L than the connection portion 66 of the ferrule). Thus, sufficient durability, air tightness and liquid tightness can be ensured at the portion. Thus, even if the interior of the tube is repeatedly washed with the brush 57 or the like, the tube can be prevented from breaking, and the tube can be expected to have a long life.

Further, since the first portion 73A of the outer layer 73, which is formed of the porous structure, covers at least a part of the outer periphery of the connection portion 66 of the ferrule, elasticity is improved at the end portion 71 of the tube. Therefore, when the end portion 71 of the tube is fixed to the connection portion 66 of the ferrule, the end portion 71 can be easily deformed, and the workability at the time of assembly can be greatly improved.

The outer layer 73 has a third portion 73C formed of a resin having a porous structure, and the third portion is located more away from the end portion 71 of the tube along the longitudinal direction L than the second portion 73B. The intermediate portion 74 of the tube is a portion disposed within the flexible sheath and is a portion to which bending stress is repeatedly applied. According to the present structure, the flexibility and elasticity of the tube can be improved by the third portion 73C, and the tube can be prevented from being bent and broken after repeated bending operations of the flexible sheath.

The first portion 73A and the second portion 73B are disposed inside the rigid body portion, and the third portion 73C is disposed inside the flexible sheath. According to the present structure, the second portion 73B having the solid structure, which has low flexibility, can be disposed inside the rigid body portion in order to shield the second portion 73B from repeated bending stress. Therefore, the tube is prevented from being broken at the second portion 73B, and the tube can be expected to have a long life.

A bending preventing portion for gradually changing the flexibility of the flexible sheath (for preventing the flexible sheath from breaking) is provided at the boundary between the rigid body portion and the flexible sheath, and the boundary between the second portion 73B and third portion 73C of the tube is disposed inside the bending preventing portion. With this structure, the bending preventing portion serves to prevent a large bending stress from being repeatedly applied to the second portion 73B of the solid structure. As a result, the tube is not damaged at the second portion 73B, and the tube can be expected to have a long life.

The first portion 73A having the porous structure can cover the entire outer periphery of the connection portion 66 of the ferrule. According to this structure, the elasticity of the end portion 71 of the tube is further improved, and the workability at the time of assembly is further improved.

The outer layer 73 may be configured such that the boundary between the first portion 73A and the second portion 73B coincides with the ends 66C and 75AA of the connection portions 66 and 75A. According to this structure, the second portion 73B is disposed away from (spaced apart from) the end portion 71 of the tube along the longitudinal direction L. As a result, the end portion 71 of the tube can be made elastic by the first portion 73A having the porous structure to improve the workability at the time of assembly, and the second portion 73B which has a solid structure and is durable can be arranged at the position which is easily scraped when washing is performed with the brush 57. Accordingly, the workability at the time of assembly can be improved, and simultaneously long life of the tube can be achieved.

A compression portion for compressing the tube and fixing the tube to the ferrule may be provided on the outer periphery of the tube. According to this structure, the first portion 73A having the porous structure can be arranged at the portion which is to be compressed by the compression portion. For this reason, when the tube is compressed and fixed by the compression portion, a large force is not required, and the burden on the assembler at the time of assembly can be reduced.

A tube fixing portion having a tubular member for compressing the tube against the ferrule may be provided on the outer periphery of the tube. According to this structure, the first portion 73A having the porous structure can be arranged at the portion which is to be compressed by the tube fixing portion. For this reason, when the tube is compressed by the tube fixing portion, a large force is not required, and the burden on the assembler at the time of assembly can be reduced.

Both the inner layer 72 and the outer layer 73 may contain a fluorine-containing resin and be formed integrally with each other. According to this structure, when the interior of the tube is washed with the brush 57 or the like, the sliding property of the fluorine-containing resin enables smooth movement of the brush 57 or the like. As a result, the workability at the time of washing can be improved, and the friction generated between the brush 57 or the like and the tube can be reduced.

Ordinarily, a tube made of fluorine-containing resin is inferior in light of bendability and flexibility. When a flexible sheath is bent with a large curvature, the tube made of fluorine-containing resin may be broken inside the flexible sheath. According to the structure described above, however, even where the inner layer 72 and the outer layer 73 contain a fluorine-containing resin, breakage of the tube due to bending can be effectively prevented.

As discussed above, the boundary between the first portion 73A and the second portion 73B may be positioned at the distal end 66C of the connection portion 66. Or, the boundary between the first portion 73A and the second portion 73B may be positioned at the end portion of the tube fixing portion.

Figure 8:
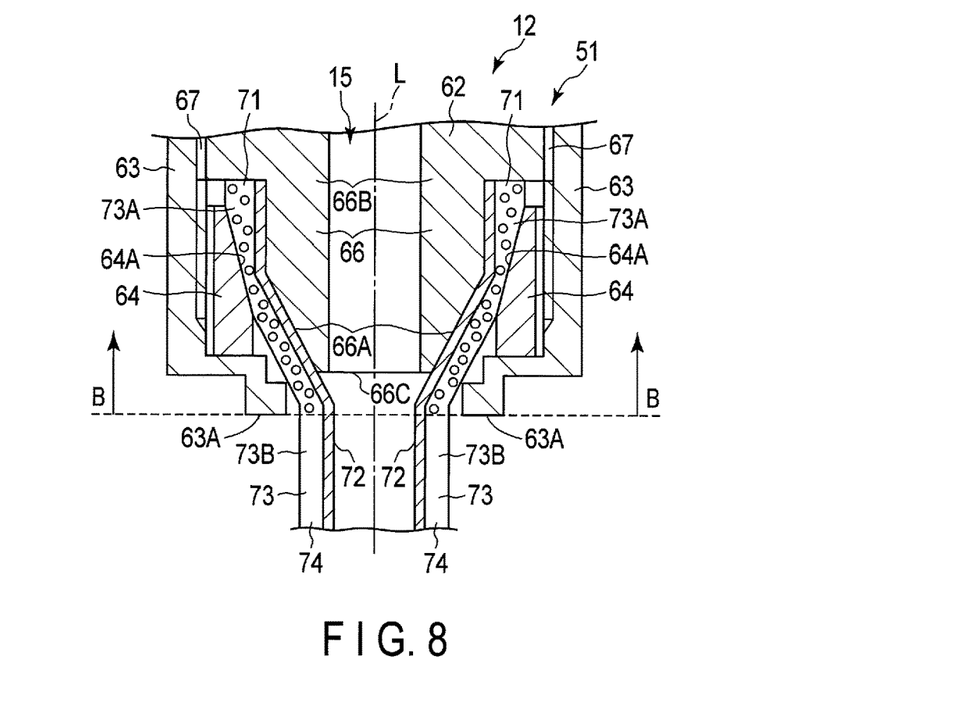
FIG. 8 is an enlarged sectional view showing a second ferrule of an endoscope system according to the disclosed embodiments.

As shown in FIG. 8, a boundary line B-B between the first portion 73A of the outer layer 73 of the first suction tube 32 and the second portion 73B thereof is provided to coincide with the end portion 63A of the nut portion 63 (tube fixing portion). This structure is applied to the connection portion 66 between the third suction tube 56 and the fourth ferrule 37. With this structure, the first portion 73A having the porous structure can be arranged at the portion to which the tube fixing portion is to be fixed. Owing to this, when a tube is compressed by the tube fixing portion, the tube can be easily deformed with a small force, and the burden on the assembler at the time of assembly can be reduced.

Figure 9:
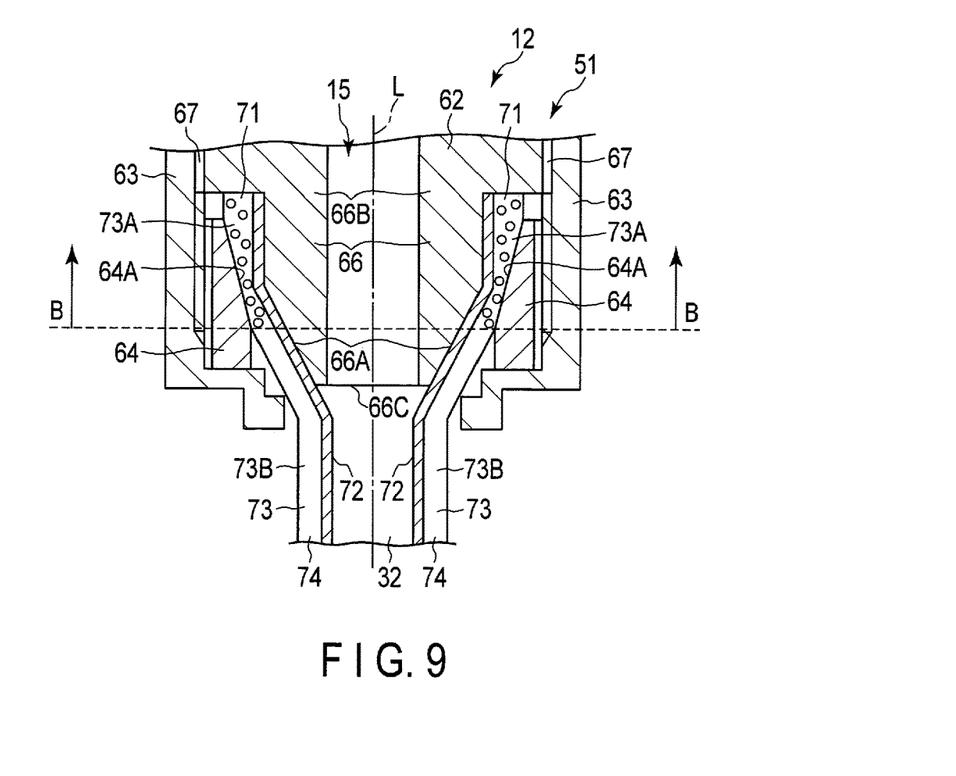
FIG. 9 is an enlarged sectional view showing a second ferrule of an endoscope system according to the disclosed embodiments.

Or, as shown in FIG. 9, the boundary line B-B between the first portion 73A and the second portion 73B may be positioned proximal to the distal end 66C of the connection portion 66. The structure shown in FIG. 9 can also be applied to the connection portion 66 between the third suction tube 56 and the fourth ferrule 37. In this case, the first portion 73A of the outer layer 73 of the third suction tube 56 covers only a part of the connection portion 66 of the fourth ferrule 37.

Figure 10:
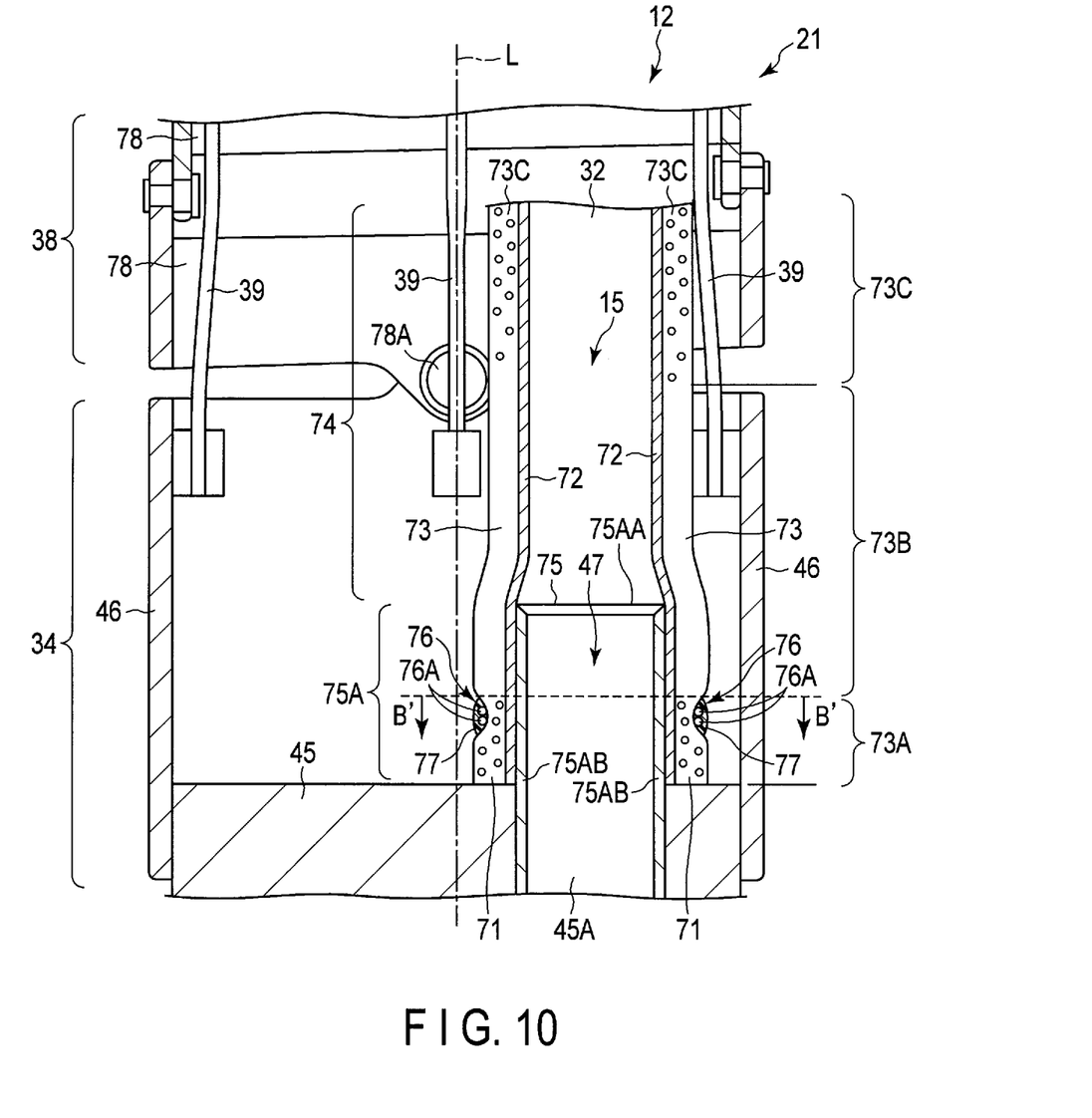
FIG. 10 is an enlarged sectional view showing a first ferrule of an endoscope system according to the disclosed embodiments.

Likewise, as shown in FIG. 10, the boundary line B'-B' between the first portion 73A of the outer layer 73 of the first suction tube 32 and the second portion 73B thereof may be positioned distal to the proximal end 75AA of the connection portion 75A. Therefore, the first portion 73A of the outer layer 73 of the first suction tube 32 covers only a part of the connection portion 75A of the first ferrule 47.

In FIGS. 9 and 10, the first portion 73A of the porous structure is provided such that it covers only a part of the connection portions 66 and 75A of the ferrules (the first ferrule 47 and the second ferrule 51); that is, the first portion 73A extends only to the portion where the compression portion (thread winding portion 76) or the tube fixing portion (nut portion 63) comes into contact with the tube (first suction tube 32). Therefore, the end portion 71 of the tube can be easily deformed, and the workability can be improved when tubes are fixed to the connection portions 66 and 75A of the ferrules.

Specifically, the first portion 73A may be disposed at a position where the tube fixing portion (nut portion 63) is fixed as shown in FIG. 9 or at a position where the compression portion (thread winding portion 76) is fixed as shown in FIG. 10. Therefore, the workability of the assembler at the time of assembly can be improved.

In addition, the second portion 73B can be disposed at a position with which the brush 57 or the like comes into contact at the time of washing, so that the tube can have sufficient durability, and the tube can be expected to have a long life.

Figure 11:
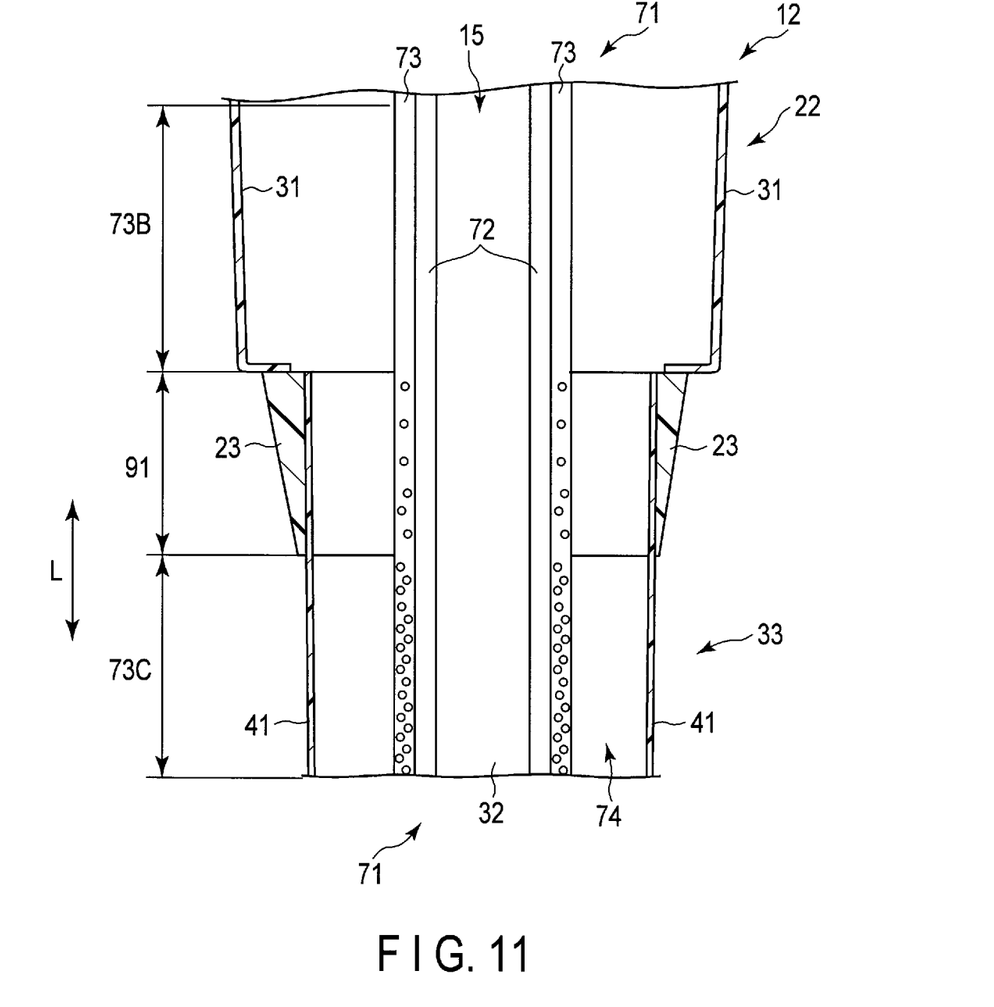
FIG. 11 is an enlarged sectional view showing a first bending preventing portion of an endoscope system according to the disclosed embodiments.

As shown in FIG. 11, the first suction tube 32 can include a transition portion 91 having an intermediate property between the porous structure and the solid structure at a position corresponding to the first bending preventing portion 23. Likewise, the third suction tube 56 can include a transition portion 91 having an intermediate property between the porous structure and the solid structure at a position corresponding to the third bending preventing portion 28.

Specifically, the first suction tube 32 has a two-layer structure including an inner layer 72 and an outer layer 73 provided outward of the inner layer 72 and integrally adhered to the inner layer 72. The first suction tube 32 includes a pair of end portions 71 and an intermediate portion 74 located between the end portions 71. The intermediate portion 74 is intended to refer to an intermediate portion of the first suction tube 32 that is other than the end portions 71. The inner layer 72 is made of a resin, e.g., PTFE, and has a solid structure entirely. The outer layer 73 is provided with a pair of first portions 73A (see FIGS. 3 and 6) provided in the vicinity of the end portions 71 and made of resin having a porous structure, a pair of second portions 73B (see FIG. 3 and FIG. 6) provided more away from the end portions 71 of the tube along the longitudinal direction L than the first portions 73A and made of a resin having solid structure, a third portion 73C provided more away from the end portion 71 of the tube along the longitudinal direction L than the second portions 73B and made of a resin having a porous structure, and a transition portion 91 provided inside the first bending preventing portion 23 and interposed between and the second portion 73B and the third portion 73C. The third portion 73C constitutes at least part of the intermediate portion 74.

The transition portion 91 has an intermediate property between the first portion 73A having the porous structure and the second portion 73B having the solid structure. The transition portion 91 has a porous structure, but the amount of bubbles contained in the transition portion 91 is, for example, about ⅓ to ⅔ of the amount of bubbles contained in the first portion 73A and the third portion 73C. That is, the porosity of the transition portion 91 is, for example, 6 to 42%, preferably 9 to 36%, and more preferably 15 to 30%. Thus, the transition portion 91 has proper flexibility.

Like the first suction tube 32, the third suction tube 56 can include a transition portion 91 located at a position corresponding to the second bending preventing portion 26 and interposed between the second portion 73B and the third portion 73C. The third suction tube 56 can also include a transition portion 91 located at a position corresponding to the third bending preventing portion 28 and interposed between the second portion 73B and the third portion 73C. The structures of these transition portions 91 are the same as the transition portions 91 provided for the first suction tube 32.

With this configuration having the transition portion, the rigidity of the tube does not abruptly change between the first portion 73A and the second portion 73B. Therefore, when a tube is attached to the ferrule at the time of assembly, or when the flexible sheath is bent during use in a medical institution, the tube is prevented from being bent or buckled at the boundary position between the second portion 73B and the third portion 73C.

Additionally, when the transition portion 91 is disposed inside the bending preventing portion, the third portion 73C having the highest flexibility is disposed at the portion corresponding to the flexible sheath to which the largest bending stress is applied, and the transition portion 91 having moderate flexibility is disposed at the portion corresponding to the bending preventing portion to which a relatively small bending stress is applied. For this reason, it is possible to realize a tube in which the portion corresponding to the bending preventing portion has durability and wear resistance against repeated washing and yet is flexible.

Although several embodiments have been described with reference to the drawings, the present invention is not limited to the embodiments described above and can be put to practical use, with the structural elements being modified without departing from the gist of the invention. Further, the structural elements of the embodiment and first to third modifications described above can be properly combined to realize one endoscope.

In connection with the embodiments, reference was made to a suction tube, but the present invention is applicable to other types of tubes to be inserted into an endoscope, including an air-supply tube, a water-supply tube and a forward water-supply tube.

REFERENCE SIGNS LIST

11 . . . Endoscope System, 12 . . . Endoscope, 23 . . . First Bending Preventing Portion, 25 . . . Universal Cord, 26 . . . Second Bending Preventing Portion, 28 . . . Third Bending Preventing Portion, 32 . . . First Suction Tube, 33 ... Pipe Portion, 37 ... Fourth Ferrule, 38 ... Bendable Section, 47 ... First Ferrule, 51 ... Second Ferrule, 52 ... Third Ferrule, 56 ... Third Suction Tube, 63 ... Nut Portion, 64 ... Pressing Ring, 66 ... Connection Portion, 66B ... Proximal End, 66C ... Distal End, 71 ... End Portion, 72 ... Inner Layer, 73 ... Outer Layer, 73A ... First Portion, 73B ... Second Portion, 73C ... Third Portion, 74 ... Intermediate Portion, 75A ... Connection Portion, 75AB ... Proximal End, 76 ... Thread Winding Portion, 82 ... Heat-Shrinkable Tube, 91 ... Transition Portion

The invention claimed is:

1. An endoscope comprising:
a flexible sheath extending in a longitudinal direction;
a rigid body portion connected to an end portion of the flexible sheath;
a ferrule provided within the rigid body portion and comprising a connection portion; and
a tube provided in the flexible sheath and including an end portion connected to the ferrule,
wherein the tube includes:
an inner resin layer having a solid structure, the inner layer extending along an entire length of the tube in the longitudinal direction; and
an outer resin layer provided on the inner resin layer and including, in order from the end portion of the tube:
a first portion having a porous structure and covering at least part of an outer periphery of the connection portion, and
a second portion having a solid structure.

2. The endoscope according to claim 1, wherein the outer resin layer further includes a third portion located on a side of the second portion away from the first portion, the third portion having a porous structure.

3. The endoscope according to claim 2, wherein the first portion and the second portion are disposed inside the rigid body portion, and the third portion is disposed inside the flexible sheath.

4. The endoscope according to claim 3, further comprising:
a bending preventing portion provided at a boundary between the rigid body portion and the flexible sheath, the bending preventing portion being configured to cause a gradual change in flexibility along a length of the flexible sheath,
wherein a boundary between the second portion and the third portion is disposed inside the bending preventing portion.

5. The endoscope according to claim 2, wherein:
the outer resin layer further includes a transition portion located between the second portion and the third portion,
the transition portion has a porous structure, and
a porosity of the transition portion is less than a porosity of the third portion.

6. The endoscope according to claim 5, further comprising:
a bending preventing portion provided at a boundary between the rigid body portion and the flexible sheath, the bending preventing portion being configured to cause a gradual change in flexibility along a length of the flexible sheath,
the transition portion is disposed inside the bending preventing portion.

7. The endoscope according to claim 5, wherein the transition portion is more flexible than the second portion and less flexible than the third portion.

8. The endoscope according to claim 5, wherein a porosity of the transition portion is in the range of 6 to 42%.

9. The endoscope according to claim 2, wherein the porosity of the first portion and the porosity of the third portion are each in the range of 20 to 70%.

10. The endoscope according to claim 2, wherein the porosity of the first portion and the porosity of the third portion are each in the range of 30 to 60%.

11. The endoscope according to claim 2, wherein the third portion is more flexible than the second portion.

12. The endoscope according to claim 11, wherein the third portion is more flexible than the first portion.

13. The endoscope according to claim 1, wherein the first portion covers the entire outer periphery of the connection portion.

14. The endoscope according to claim 1, wherein the first portion covers only the part of the outer periphery of the connection portion.

15. The endoscope according to claim 1, further comprising:
a compression portion provided on an outer periphery of the tube and configured to press the tube against the ferrule, thereby fixing the tube to the ferrule.

16. The endoscope according to claim 1, further comprising:
a tube fixing portion provided on an outer periphery of the tube, the tube fixing portion including a tubular member configured to compress the tube against the ferrule.

17. The endoscope according to claim 16, wherein a boundary between the first portion and the second portion is positioned at an end of the tube fixing portion away from the end portion.

18. The endoscope according to claim 1, wherein the inner resin layer and the outer resin layer both contain a fluorine-containing resin and are formed integrally with each other.

19. The endoscope according to claim 1, wherein the first portion is more compressible than the second portion.

20. An endoscope comprising:
a flexible sheath extending in a longitudinal direction;
a rigid body portion connected to an end portion of the flexible sheath;
a ferrule provided within the rigid body portion and comprising a connection portion; and
a tube provided in the flexible sheath and including an end portion connected to the ferrule,
wherein the tube includes, in order from the end portion of the tube:
a first portion covering at least a part of an outer periphery of the connection portion and including an inner resin layer having a solid structure, and an outer resin layer provided on the inner resin layer and having a porous structure; and
a second portion formed entirely of a solid resin structure resin.

* * * * *